Figure 1:
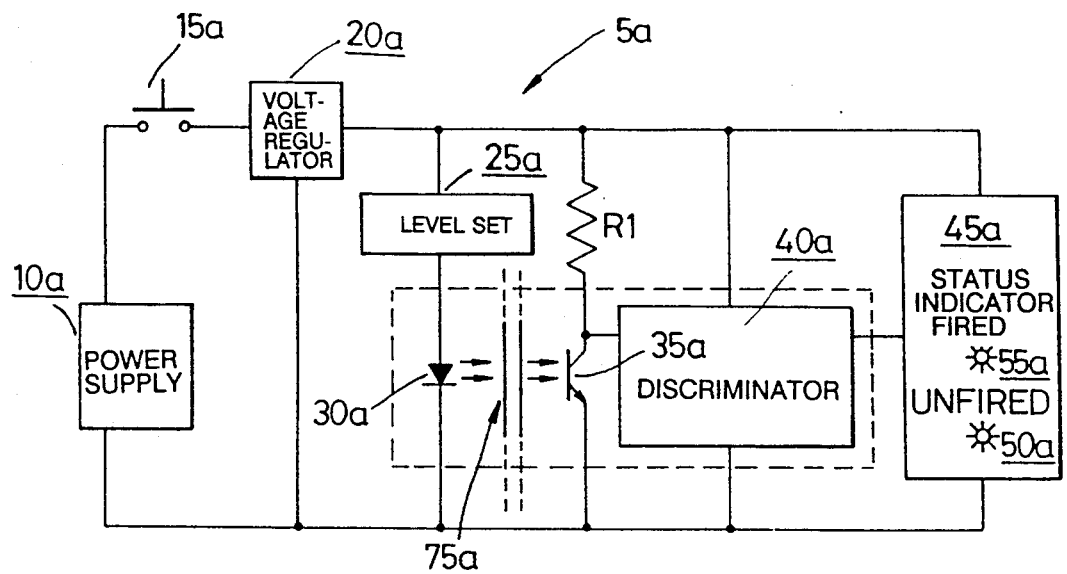

United States Patent [19]

Gordon

[11] Patent Number: 5,185,528
[45] Date of Patent: Feb. 9, 1993

[54] BLASTING ACCESSORY

[75] Inventor: Kenneth A. Gordon, Ayr, Scotland

[73] Assignee: Imperial Chemical Industries PLC, London, England

[21] Appl. No.: 741,658

[22] Filed: Aug. 7, 1991

[30] Foreign Application Priority Data

Aug. 17, 1990 [GB] United Kingdom ............ 9018137

[51] Int. Cl.[5] .............................................. G01N 21/35
[52] U.S. Cl. ................................... 250/341; 102/200; 250/358.1
[58] Field of Search ....................... 250/341, 358.1; 102/200, 275.8

[56] References Cited

U.S. PATENT DOCUMENTS 4,403,143 9/1983 Walker et al. ............... 102/275.8

Primary Examiner—Carolyn E. Fields
Attorney, Agent, or Firm—Cushman, Darby & Cushman

[57] ABSTRACT

The invention provides a blasting accessory (5a, 5b, 5c) and related method which can be used to test whether a shock/signal tube (75a, 75b, 75c) has been fired and/or to distinguish one type of tube (75c) from another. This addresses a problem in the Prior Art, namely that it is difficult for a field operator to distinguish between live and fired tubing or different types of tubing. The accessory (5a, 5b, 5c) comprises an IR source (30a, 30b, 30c) spaced from and facing a Si photodetector (35a, 35b, 35c). An output of the detector (35a, 35b, 35c) is connected via discrimination circuitry (40a, 40b 40c) to either status indication means (40a, 40b) or proportional indication means (45c). In use, a shock/signal tube (75a, 75b, 75c) is located between the source (30a, 30b, 30c) and detector (35a, 35b, 35c). The amount of radiation passing through the tube (75a, 75b, 75c) in its transverse direction provides an indication of whether the tube (75a, 75b, 75c) has been fired and/or what type of tube (75c) is under test.

14 Claims, 3 Drawing Sheets

BLASTING ACCESSORY

This invention concerns blasting operations in which shock tube or signal tube transmission systems are used, and in particular relates to a blasting accessory and related method which can be used to test whether a shock/signal tube has been fired and/or to distinguish one type of tubing from another.

Shock tubes and signal tubes are classes of low-energy fuse used in blasting systems for transmitting an initiation signal from one point to another (usually from one detonator or pyrotechnic delay device to another), the tubes being constructed of plastic, usually extruded and unreinforced, and containing a particular detonating or rapid reacting pyrotechnic composition distributed substantially uniformly along its central core at relatively low loadings compared to common detonating cords.

Shock tube, for example, will typically consist of extruded plastic tube of internal diameter around 1 mm with a core loading of, say, HMX/Al (94:6 parts by weight) of below 20 mg/m. Signal tube designed for lower signal transmission speeds (i.e. significantly below 2 km/s) will have similar dimensions, and will contain a rapid reacting pyrotechnic composition comprising a metal fuel and a powerful inorganic oxidising agent (e.g. $Si/BaO_2$) typically at a core loading of around 20 mg/m to 100 mg/m.

In field or mine situations it is not always immediately apparent to a blast engineer that a particular tube has fired merely from visual inspection of the still intact tube. This is in part because the visible colour change of the core material upon detonation or reaction may not be significant, especially at low core loadings. A further reason is that accessories producers prefer to supply coloured products and so the plastic of the shock/signal tube usually will be self-coloured, thus masking to a significant degree any core colour change that might otherwise have been perceptible. Additionally, natural or artificial light levels, especially underground, are not always at an intensity or spectral breadth conducive to perceiving a colour change in core material.

It is therefore an object of the present invention to obviate or mitigate the aforementioned problems.

It is a further object of the present invention to provide a blasting accessory and related method which can be used to test whether a shock/signal tube has been fired and/or to distinguish one type of tubing from another.

Accordingly, one aspect of the present invention provides a blasting accessory to test whether a shock/signal tube has been fired comprising a source of electromagnetic radiation spaced from and facing a detonator suitable for detecting the radiation, an output of the detector being connected via discrimination circuitry, responsive to the output, to status indication means, wherein, in use, the shock/signal tube is located between the source and detector such that the amount of radiation emitted by the source passing through the tube in its transverse direction falling on the detector, and therefore the status of the status indication means, is dependent upon whether or not the tube has been fired.

A second aspect of the invention provides a blasting accessory to distinguish between different types of shock/signal tube comprising a source of electromagnetic radiation spaced from and facing a detector suitable for detecting the radiation, an output of the detector being connected via discrimination circuitry, responsive to the output, to proportional indication means, wherein, in use, a shock/signal tube is located between the source and detector such that the amount of radiation emitted by the source passing through the tube in its transverse direction falling on the detector, and therefore the status of the proportional indication means, is dependent upon the type of tube.

The blasting accessory may both test whether a shock/signal tube has been fired and distinguish between different types of shock/signal tube.

Preferably also, the electromagnetic radiation is in the infra-red, IR, range.

Preferably also, the source is a gallium arsenide, GaAs, light emitting diode, LED, or laser diode and the source is a silicon, Si, photodetector.

It is also preferable that the source, detector and discrimination circuitry are provided within an integrated package.

It is further preferable that the blasting accessory is packaged within a box for hand held use, the space between the source and detector being provided on the external surface of the box by means of a protruding slotted receptor in which the source and detector are packaged.

Preferably also, a cover member is provided which can be placed across the protruding slotted receptor, in use, to shield the tube in the space from ambient radiation.

Preferably the status indication means is in the form of first and second usually unlit indicators, wherein, in use, the first indicator lights up if the tube has been fired, and the second indicator lights up if the tube has not been fired.

Preferably also, the proportional indication means is in the form of a moving coil meter.

Alternatively the proportional indication means may be in the form of a digital meter or a bar of LEDs.

According to a third aspect of the present invention there is provided a method of testing whether a shock/signal tube has been fired comprising placing the shock/signal tube in a space between a source of electromagnetic radiation facing a detector suitable for detecting the radiation, detecting the amount of radiation emitted by the source passing through the tube in its transverse direction falling on the detector, and using an output of the detector to drive discrimination circuitry responsive to the output and connected to status indication means, the status of the status radiation means being dependent upon whether or not the tube has been fired.

According to a fourth aspect of the present invention there is provided a method of distinguishing between types of shock/signal tube comprising placing a shock/signal tube in a space between a source of electromagnetic radiation facing a detector suitable for detecting the radiation, detecting the amount of radiation emitted by the source passing through the tube in its transverse direction falling on the detector, and using an output of the detector to drive discrimination circuitry responsive to the output and connected to proportional indication means, the status of the proportional indication means being dependent upon the type of tube.

Figure 2:
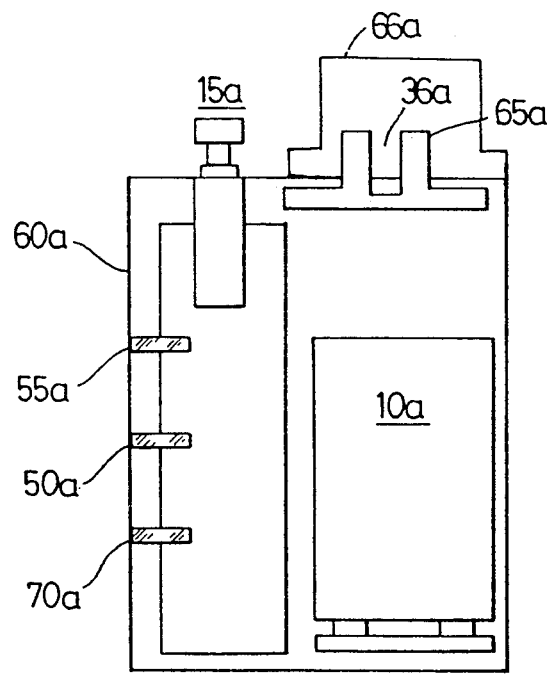
Figure 3:
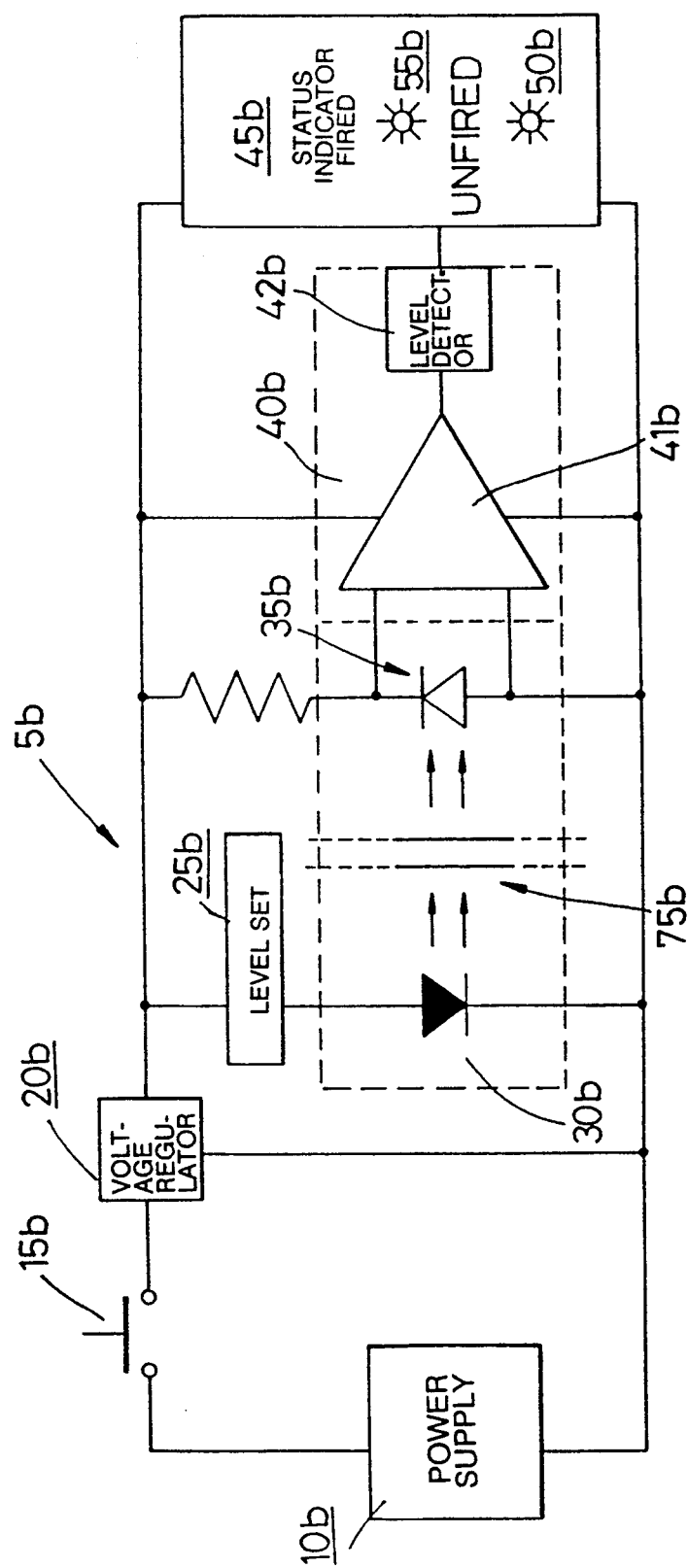
Figure 4:
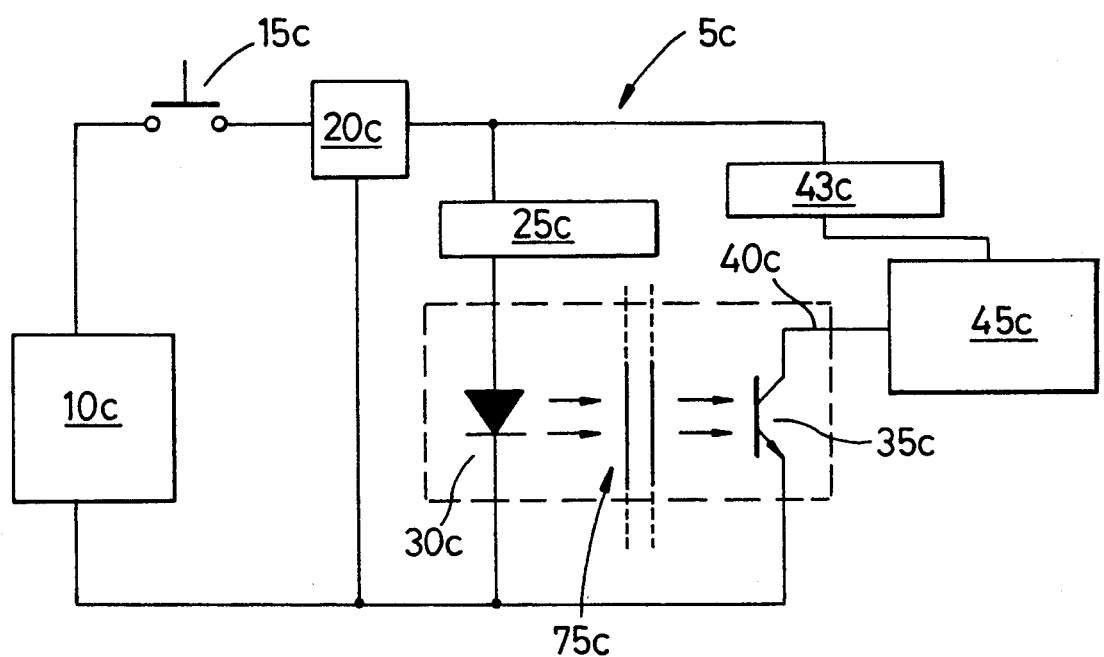

The invention will now be described by way of example only, with reference to the accompanying drawings which are:

FIG. 1: a schematic circuit diagram of a blasting accessory according to a first embodiment of the present invention;

FIG. 2: a schematic from view of a box packaging the blasting accessory of FIG. 1;

FIG. 3: a schematic circuit diagram of a blasting accessory according to a second embodiment of the present invention; and FIG. 4: a schematic circuit diagram of a blasting accessory according to a third embodiment of the present invention.

Referring to FIGS. 1 and 2, there is provided a first embodiment of a blasting accessory according to the present invention, generally designated 5a, which can test whether or not a shock/signal tube has been fired.

The blasting accessory 5a comprises a power supply 10a connected in series with an on-off switch 15a and a voltage regulator 20a. The power supply 10a is preferably in the form of a battery or batteries.

Connected in parallel with the power supply 10a, switch 15a and voltage regulator 20a are the following components: a level set device 25a in series with a source of electromagnetic radiation 30a; a resistor R1 in series with a photodetector 35a; discriminator circuitry 40a; and status indication means 45a.

The level set device 25a would normally be a potentiometer which can be used to vary the amount of drive current delivered to the source 30a. This enables the output of the source 30a to be set at a desired operational level which will be dependent upon the type of transmission tube being tested, the optimum response band of the photodetector 35a and, if desired, the level of ambient radiant radiation also incident upon the photodetector 35a.

The source 30a will typically be of the gallium arsenide (GaAs)/ aluminium gallium arsenide (AlGaAs) light emitting diode (LED) or laser diode type having an infra-red (IR) peak emission wavelength of the order of 880 nm to 935 nm. This type of source 30a is particularly suitable because even the low core loadings of shock/signal tube are very visible in the IR region.

The detector 35a is spaced from and facing the source 30a across a space 36a. Any suitable detector 35a may be used. However, for this IR region normally a silicon, Si, photodetector is used. In this embodiment the detector 35a is a Si phototransistor.

The discrimination circuitry 40a is suitably connected in parallel with the supply 10a, switch 15a and regulator 20a, and also to the collector of the Si phototransistor 35a and to the status indication means 45a.

The details of the discrimination circuitry 40a are not given herein as these would be apparent to anyone skilled in the relevant art. The circuitry 40a is organised, however, so that if the signal detected by the detector 35a is below a certain threshold, i.e. if the tube is live (has not been fired) a first signal is given out by the circuitry 40a, while if the signal is above the threshold, i.e. if the tube has been fired, a second signal is given out. With shock tubes most of the core material is dissipated as gas on firing. With signal tubes the proportion of residual solid material will be much greater. Therefore one would expect that more of the radiation from the source would be absorbed by fired signal tube than by shock tube.

The dotted line in FIG. 1 around the source 30a, detector 35a and discriminator circuitry 40a indicates that they may be formed as an integrated device. Examples of combined source/detector pairs 30a, 35a in an integrated package are Honeywell HOA 87 series device with no internal electronics, or HOA 2001 with internal electronics and Schmitt output as used in a second embodiment of the invention as shown in FIG. 3.

The status indication means 45a are in the form of a pair of light emitting diodes LEDs 50a and 55a. The first LED 50a lights up if the discriminator circuitry 40a gives out the first signal indicating that the tube is live, and the second LED 55a lights up if the discriminator ciruitry 40a gives out the second signal indication that the tube has been fired.

Referring to FIG. 2 for hand-held use, the accessory 5a is housed in a moulded plastic hand-set box 60a having a removable cover (not shown) to allow access to a battery compartment to enable battery replacement.

Further the source 30a and detector 35a are provided on opposing and spaced internal surfaces of a slotted receptor 65a located on one edge of the box 60a.

In order to shield the source 30a and detector 35a from ambient radiation, e.g. bright sunlight, the slotted receptor 65a may have a pivotally releasable cover (66a) on an upper surface thereof. This would shield the Si photodetector 35a when the device was not in use, and could also, if suitably designed, be returnable to its fully closed position for tube testing, if desired.

The LEDs 50a and 55a are suitably located on an edge of the box, and a further LED 70a also provided thereon. The LED 70a is suitably electrically connected to the battery 10a to indicate if the battery 10a becomes drained of power, as is conventional on many electrical devices.

In use a length of tube 75a is placed within the space 36a provided in the slotted receptor 65a. When power is supplied to the source 30a, IR radiation travels to the detector 35a transversely through the tube 75a. If the tube 75a is live then much of the radiation is absorbed by the coating within the tube 75a. Accordingly, a low signal (below threshold) is output from the Si photodetector 35a, and a first signal output from the discriminator circuitry 40a causes the "unfired" LED 50a to illuminate.

If, however, the tube 75a has been fired then less radiation is absorbed by the coating within the tube 75a. Accordingly a high signal (above threshold) is output from the Si photodetector 35a, and a second signal output from the discriminator circuitry 40a causes the "fired" LED 55a to illuminate.

An operator may carry pieces of fired and live tubing so that he may confirm the settings of the device. Further, the device may be field calibrated if desired by suitable fine adjustment of the ciruitry.

Referring to FIG. 3, there is provided a second embodiment of a blasting accessory according to the present invention, generally designated 5b, which can test whether or not a shock/signal tube has been fired.

This second embodiment is substantially the same as the first embodiment except that the detector 35b used in the second embodiment is a Si photodiode, and that the discriminator ciruitry 40b comprises an amplifier 41b the input of the amplifier 41b being connected to the Si photodiode 35b, the output of the amplifier 41b being connected to the input of a voltage level detector 42b which may be in the form of a Schmitt trigger. The output of the voltage level detector 42b is connected to the input of the status indication means 45b in a similar manner as in the first embodiment.

The function and operation of the second embodiment is similar to that of the first embodiment, and therefore needs no further explanation.

Referring to FIG. 4, there is provided a third embodiment of a blasting accessory according to the present invention, generally designated 5c, which can test whether or not a shock/signal tube has been fired and also distinguish between different type of shock/signal tube.

The blasting accessory 5c comprises a power supply 10c connected in series with an on-off switch 15c and a voltage regulator 20c.

Connected in parallel with the power supply 10c, switch 15c to voltage regulator 20c are the following components: a level set device 25c in series with a source of electromagnetic radiation 30c; a scale adjust facility 43c in series with proportional indication means 45c, discriminator circuitry 40c and a photodetector 35c.

The scale adjust facility 43c can be in the form of a potentiometer. Further the proportional indication means 45c can be in the form of a moving coil meter, a digital meter or a bar of LEDs.

The discrimination circuitry 40c in this embodiment is merely a connection between the proportional indication means 45c and the collector connection of the phototransistor forming the photodetector 35c.

In use, a length of tube 75c is placed between the source 30c and the detector 35c. When power is supplied to the source 30c, IR radiation travels to the detector transversely through the the tube 75c. If the tube 75c is live then much of the radiation is absorbed by the coating within the tube 75c. Accordingly a low signal is output from the Si phototransistor 35c, and a first signal travelling through the discriminator circuitry 40c causes the proportional indication means 45c to show a corresponding reading. If, however, the tube 75c has been fired then less radiation is absorbed by the coating within the tube 75c. Accordingly a high signal is output from the phototransistor 35c, and a second signal travels through the discriminator circuitry 40c causing the proportional indication means 45c to show another corresponding reading.

If various types of tubes 75c are tested then the amount of radiation absorbed by the tubing 75c, and hence the signal output from the Si phototransistor 35c, the signal travelling through the discrimination circuitry 40c and the reading on the proportional indication means 45c will be dependent upon the core loading of the tube 75c. It can therefore be seen that the proportional indication means 75c can be calibrated so that an operator can easily identify various types of tube 75c and also whether or not the tube 75c has been fired.

In summary, the Applicants have devised a simple battery run hand operated blasting accessory 5a, 5b, 5c which a plant engineer can easily carry about his person—say clipped to a waist belt or in a breast pocket or work bag—which will enable him to distinguish fired signal/shock tube from live (unfired) tube and/or differentiate one type of tube from another having a different core loading, depending on how the circuitry is designed.

It should, however, be appreciated that the embodiments of the invention hereinbefore described are given by way of example only, and are in no way meant to limit the scope of the invention. Particularly, it should be understood that although the specific embodiments employ GaAs/AlGaAs sources and Si photodetectors, any source/detector pairs operating at a suitable wavelength can be used dependent upon the transmission properties of the tube under test.

I claim:

1. A blasting accessory to test whether a shock/signal tube has been fired comprising: a source of electromagnetic radiation, a detector suitable for detecting the radiation spaced from and facing the source, discrimination circuitry connected to an output of the detector, responsive to the output and, status indication means connected to the output of the detector via the discrimination circuitry, wherein, in use, the shock/signal tube is located between the source and detector such that the amount of radiation emitted by the source passing through the tube in its transverse direction falling on the detector, and therefore the status of the status indication means, is dependent upon whether or not the tube has been fired.

2. A blasting accessory to test whether a shock/signal tube has been fired and/or to distinguish between different types of shock/signal tube comprising: a source of electromagnetic radiation, a detector spaced from and facing the source suitable for detecting the radiation, discrimination circuitry, connected to an output of the detector and responsive to the output, the proportional indication means connected to the output of the detector via the discrimination circuitry, wherein, in use, the shock/signal tube is located between the source and detector such that the amount of radiation emitted by the source passing through the tube in its transverse direction falling on the detector, and therefore the status of the proportional indication means, is dependent upon whether or not the tube has been fired and the type of tube.

3. A blasting accessory as claimed in claim 1, wherein the electromagnetic radiation is in the infra-red range.

4. A blasting accessory as claimed in claim 3, wherein the source is a gallium arsenide light emitting diode or laser diode and the detector is a silicon Si photodetector.

5. A blasting accessory as claimed in claim 4, wherein the source, detector and discrimination circuitry are provided within an integrated package.

6. A blasting accessory as claimed in claim 2, wherein the elecromagnetic radiation is in the infra-red range.

7. A blasting accessory as claimed in claim 6, wherein the source is a gallium arsenide light emitting diode or laser diode and the detector is a silicon photodetector.

8. A blasting accessory as claimed in claim 7, wherein the source, detector and discrimination circuitry are provided within an integrated package.

9. A blasting accessory as claimed in any preceding Claim, wherein the blasting accessory is packaged within a box for hand held use, the space between the source and detector being provided on the external surface of the box by means of a protruding slotted receptor in which the source and detector are packaged.

10. A blasting accessory as claimed in claim 9, wherein a cover member is provided which is movable to a position across the protruding slotted receptor to shield the tube in the space from ambient radiation.

11. A blasting accessory as claimed in claim 1, wherein the status indication means is in the form of first and second usually unlit indicators, wherein, in use, the first indicator lights up if the tube has been fired, and the second indicator lights up if the tube has not been fired.

12. A blasting accessory as claimed in claim 2, wherein, the proportional indication means is in the form of a moving coil meter, a digital meter or a bar of LEDs.

13. A method of testing whether a shock/signal tube has been fired comprising: placing the shock/signal tube in a space between a source of electromagnetic radiation facing a detector suitable for detecting the radiation, detecting the amount of radiation emitted by the source passing through the tube in its transverse direction falling on the detector, and using an output of the detector to drive discrimination circuitry responsive to the output and connected to status indication means, the status of the status radiation means being dependent upon whether or not the tube has been fired.

14. A method of testing whether a shock/signal tube has been fired and distinguishing between types of shock/signal tube comprising: placing the shock/signal tube in a space between a source of electromagnetic radiation facing a detector suitable for detecting the radiation, detecting the amount of radiation emitted by the source passing through the tube in its transverse direction falling on the detector, and using an output of the detector to drive discrimination circuitry responsive to the output and connected to proportional indication means, the status of the proportional indication means being dependent upon whether the shock/signal tube has bee fired and the type of tube.

* * * * *